US00PP19041P2

(12) United States Plant Patent
Sheehan

(10) Patent No.: US PP19,041 P2
(45) Date of Patent: Jul. 22, 2008

(54) GRAPEVINE 'SHEEGENE-6'

(50) Latin Name: *Vitis vinifera*
Varietal Denomination: Sheegene-6

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 0 days.

(21) Appl. No.: 11/708,800

(22) Filed: Feb. 20, 2007

(51) Int. Cl.
*A01H 5/00* (2006.01)

(52) U.S. Cl. ..... Plt./205
(58) Field of Classification Search ..... Plt./205
See application file for complete search history.

*Primary Examiner*—Annette H Para
(74) *Attorney, Agent, or Firm*—Baker Manock & Jensen, PC; Eric C. Cole

(57) ABSTRACT

A new and distinct variety characterized by large, red-colored nearly seedless grapes that ripen in late July to early August, several weeks later than the Flame Seedless Grape (unpatented), when grown in the San Joaquin Valley of Central California. The grapes of this new variety are produced on strong stems and branches and are well adapted to commercial handling.

1 Drawing Sheet

Latin name of the genius and species of the plant claimed: The claimed plant relates to a new and distinct variety of *Vitis vinifera* to be known as 'Sheegene-6'.

Variety denomination:

This invention relates to a new discovery and asexual propagation of this new variety of *Vitis vinifera*. The new variety was first hybridized by Timothy P. Sheehan of Porterville, Calif. in the Spring of 2000. The pollen parent is 'Princess' (unpatented) and the seed parent is 'Red Globe' (U.S. Plant Pat. No. 4,787). Date of first flowering occurred in May 2003. The new variety was asexually propagated in the dormant season of 2003/2004, grafted on 'Harmony', virus-free rootstock new Fowler, Calif. Two vines were planted at that time in a variety block of *Vitis Vinifera* located near Fowler, Calif. on the west side of Thompson Road, north of Adams Road, in the San Joaquin Valley of Central California. The red-colored seedless grapes produced by the new variety are larger in size than the 'Flame Seedless' (unpatented) and mature approximately two weeks later. The new variety has been shown to maintain its distinguishing characteristics through asexual propagation.

BACKGROUND OF THE INVENTION

The present invention relates to a new and distinct variety of grape which will hereinafter be denominated as 'Sheegene-6' and more particularly to a grapevine which produces a large, red-colored nearly seedless grape which is mature for commercial harvesting and shipment during the fourth week of July to the first week of August in the San Joaquin Valley of Central California. The new invention most closely resembles 'Flame Seedless' (unpatented) but it produces a larger grape that is very sweet, has excellent flavor, and matures approximately two weeks later.

SUMMARY OF THE INVENTION

The 'Sheegene-6' grapevine is characterized by producing a large, red-colored nearly seedless grape with excellent flavor that is mature for harvesting and shipment during the fourth week of July to the first week of August in the San Joaquin Valley of Central California. The new variety can be compared to the Flame Seedless (unpatented) but the grapes mature about two weeks later, among other distinguishing characteristics.

BRIEF DESCRIPTION OF THE DRAWING

The accompanying drawing is a color photograph that displays mature leaves, small leaves with tendrils, clusters of mature and immature grapes, four grapes cut in half displaying the color of the flesh and the shape of the berries, in addition to a short mature branch displaying its color.

DETAILED BOTANICAL DESCRIPTION

Referring more to the horizontal description of the new and distinct variety of grapevine, the following description has been observed under the ecological conditions prevailing at the origin vineyard located near Fowler, Calif. in the San Joaquin Valley of Central California.

All major color designations are by reference to the Dictionary of Color by Maerz and Paul, First Edition, published in 1930. Common color names are also used in several instances.

Vine:

*Size.*—Medium to large for a four year old vine.
*Vigor.*—Very good. Figure — Form: With wide cordons forming a "T" shape.
*Production.*—Very good.
*Regularity of bearing.*—Regular.

Trunk:

*Size.*—Medium, 15.24 cm (6 inches) in circumference, 25 inches above graft.
*Surface texture.*—Rough, shaggy.
*Color.*—P1.7 E10 Chestnut Brown Stone.
*Mature cane color.*—P1.14 L 12 Sudan br.
*Nodes.*—Six on canes, 59.7 cm (23½ inches) long.
*Length between nodes.*—10.16 cm (4 inches). Lenticels — Number: 0. Lenticels — Size: 0. Shoots — Size: Medium. Shoots — Length: 5.08 cm (2.0 inches). Shoots — Shape: Drooping. Tendrils — Number: One at node. Tendrils — Size: 4 cm (10.16 inches) in length. Tendrils — Location: At node.

Tendrils — Form: Bifurcate. Tendrils — Texture: Firm.

*Bud shape.*—Convex.

*Bud size.*—5 mm (0.20 inches) in length; 7 mm (0.28 inches) in width.

*Buds fruitfulness.*—Very good.

Branches:

*Size.*—Medium, 5.08 cm (2 inches) in circumference.

*Cordons.*—101.6 cm (40 inches) on one side of trunk, 81.28 cm (32 inches) on other side of trunk. Color — One year or older wood: P1. 7F9 Kaffa Hamstead Brown. Color — Immature Branches: P1.20 L5 — Lettuce gr.

Leaves:

*Size.*—Large. Density: Dense.

*Average length.*—13.5 cm (5.59 inches).

*Average width.*—17.9 cm (7.05 inches).

*Form.*—Pentagonal. Texture — Upper Surface: Smooth. Texture — Lower Surface: Glabrous. Color — Upwardly Disposed Surface: P1.23 J8 Mt. Vernon green. Color — Lower Disposed Surface: P1.20 K7 Near Piquant green. Color — Leaf Vein: P1.20 K6 — Piquant gr.

*Glandular characteristics.*—0.

*Petiole size.*—Large.

*Petiole length.*—16.5 cm (6.5 inches).

*Petiole thickness.*—3 mm (0.12 inches). Petiole Sinus — Form: Upside down U-shape.

*Lobes.*—Four.

*Tooth size.*—13 mm (0.51 inch) in length, 12 mm (0.47 inches) in width. Tooth — Number: Three large between lobes. Tooth — Shape: Convex.

Inflorescence:

*Size.*—Large, 160 to 192 mm (6.30 to 7.56 inches). Number Borne — Per Spur: Two to three (average). Number Borne — Per Vine: At least 30.

Flowers:

*Flower buds.*—Size: Small.

*flower buds.*—Surface: Glabrous.

*Flower buds.*—Generally: Profuse.

*Date of bloom.*—May 12, 2002.

*Date of full bloom.*—May 15, 2006.

*Size of bloom.*—4 mm (0.16 inches).

*Petal color.*—P1.7 C9 Chicle.

*Pistol color.*—P1.20 L5 Lettuce green.

*Date of first visible berries.*—May 17, 2006.

*Size.*—2 to 3 m (0.08 to 0.12 inches).

Fruit:

*Solids.*—21.2° Brix.

*Acid.*—0.35.

*Sugar/Acid ratio.*—54.3.

*Juice pH.*—3.73.

*Seeds.*—Rudimentary.

*Seed numbers.*—Two.

*Capsium pedicel.*—6 mm (0.24 inches).

*Berry weight.*—9.94 grams.

*Juice color.*—P1.1 C1.

*Size.*—Large. Cluster — Size: Large. Cluster — Average Length: 29.5 cm (11.22 inches), not including main stem of cluster). Cluster — Average Diameter at Greatest Width: 22.5 cm (8.8 inches). Cluster — Weight: 1,590.4 grams (3½ lbs.).

*Compact.*—Compact.

*Cluster Form.*—Conical. Stems — Generally: Medium; 8 cm (3.15 inches). Stem — Caliper: 7 mm (0.28 inches).

*Berry form.*—Globular.

*Berry number.*—Approximately 158 per bunch. Berry Size — Average Dimension in Longitudinal Axis: 21 mm (0.83 inches). Berry Size — Average Dimension in Transverse Axis: 22 mm (0.87 inches).

Skin:

*Thickness.*—Thin.

*Tendency to crack.*—None known.

*Blush color.*—P1.55 H9 Gooseberry.

*Ground color.*—P1.53 B3 Rose Quartz +.

*Pulp.*—Clear.

*Lenticels.*—0.

Flesh:

*Color.*—P1.53 F6.

*Juice production.*—Good.

*Flavor.*—Very good.

*Aroma.*—Very mild.

*Texture.*—Somewhat firm.

*Ripening.*—Even.

*Eating quality.*—Very good.

*Harvesting.*—Late July to early August.

*Shipping and handling qualities.*—Medium.

Having thus described and illustrated our new variety of grapevine, we claim:

1. A new variety of grapevine to be known as Sheegene-6 and parts thereof, substantially as illustrated and described, characterized principally by its production of large, red-colored nearly seedless grapes, that mature approximately two weeks later in the season of ripening than does the Flame Seedless Grape (unpatented) which it resembles.

* * * * *

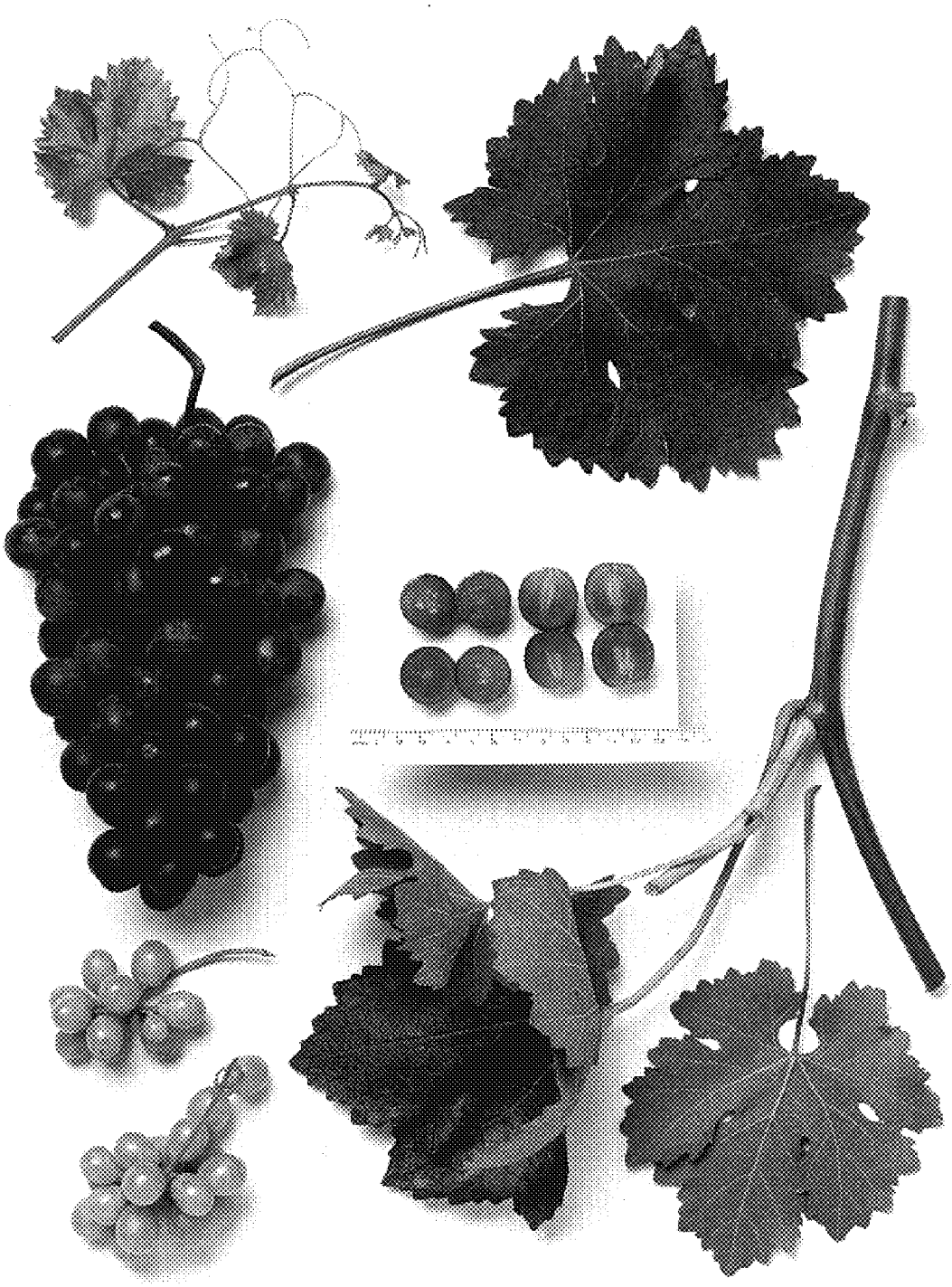

UNITED STATES PATENT AND TRADEMARK OFFICE

CERTIFICATE OF CORRECTION

PATENT NO. : PP19,041 P2
APPLICATION NO. : 11/708800
DATED : July 22, 2008
INVENTOR(S) : Timothy P. Sheehan It is certified that error appears in the above-identified patent and that said Letters Patent is hereby corrected as shown below:

Column 1, lines 8 to 9, "'Princess' (unpatented)" should be changed to --'Flame Seedless' (unpatented)--.

Signed and Sealed this
Third Day of April, 2012

David J. Kappos

David J. Kappos
*Director of the United States Patent and Trademark Office*